(12) United States Patent
McIntosh et al.

(10) Patent No.: US 11,559,685 B2
(45) Date of Patent: Jan. 24, 2023

(54) MODULAR NEUROLOGICAL SCREENING ADAPTER SYSTEM FOR INTRAOPERATIVE TESTING AND PATIENT-WORN TRIALING

(71) Applicant: BIOTRONIK SE & CO. KG, Berlin (DE)

(72) Inventors: David McIntosh, Wilsonville, OR (US); Andrew B. Kibler, Lake Oswego, OR (US); Lauren Kraiter, Tigard, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 375 days.

(21) Appl. No.: 16/711,496

(22) Filed: Dec. 12, 2019

(65) Prior Publication Data

US 2021/0085975 A1 Mar. 25, 2021

Related U.S. Application Data

(60) Provisional application No. 62/793,912, filed on Jan. 18, 2019.

(51) Int. Cl.
*A61N 1/36* (2006.01)
*A61N 1/372* (2006.01)
*A61N 1/04* (2006.01)
*A61N 1/05* (2006.01)

(52) U.S. Cl.
CPC ....... *A61N 1/36062* (2017.08); *A61N 1/0456* (2013.01); *A61N 1/0551* (2013.01); *A61N 1/37241* (2013.01)

(58) Field of Classification Search
CPC .............. A61N 1/36062; A61N 1/0456; A61N 1/0551; A61N 1/37241; A61N 1/3752
See application file for complete search history.

(56) References Cited

U.S. PATENT DOCUMENTS 5,720,771 A * 2/1998 Snell .................... A61B 5/0031
600/509
6,295,475 B1 * 9/2001 Morgan ................. A61N 1/056
607/122

(Continued)

*Primary Examiner* — Alyssa M Alter
(74) *Attorney, Agent, or Firm* — Laurence A. Greenberg; Werner H. Stemer; Ralph E. Locher (57) ABSTRACT

An adapter system connects to implantable electrode leads. The adapter system has the pulse generator configured to generate electrical stimulation pulses and has a first connector member. The adapter has a housing containing two receptacles. Each receptacle receives an end portion of an electrode lead to establish an electrical connection between the adapter and the electrode lead. The adapter contains a second connector member configured to engage with the first connector member to establish a mechanical connection between the housing and the pulse generator and an electrical connection between the pulse generator and the electrode lead. A test cable electrically connects the pulse generator to the electrode leads for testing the electrode leads. The test cable contains a first connector member configured to engage with the second connector member to establish an electrical connection. The test cable contains a second connector member configured to engage with the first connector member.

16 Claims, 7 Drawing Sheets

(56) References Cited

U.S. PATENT DOCUMENTS

| | | | |
|---|---|---|---|
| 6,553,263 B1 * | 4/2003 | Meadows | A61N 1/3787 607/33 |
| 6,609,029 B1 * | 8/2003 | Mann | A61N 1/3752 607/37 |
| 2003/0077943 A1 * | 4/2003 | Osypka | H01R 31/02 439/623 |

* cited by examiner

MODULAR NEUROLOGICAL SCREENING ADAPTER SYSTEM FOR INTRAOPERATIVE TESTING AND PATIENT-WORN TRIALING

CROSS-REFERENCE TO RELATED APPLICATION

This application claims the priority, under 35 U.S.C. § 119(e), of provisional application No. 62/793,912, filed Jan. 18, 2019; the prior application is herewith incorporated by reference in its entirety.

BACKGROUND OF THE INVENTION

Field of the Invention

The present invention relates to an adapter system for connecting a pulse generator to implantable electrode leads for neurostimulation.

Neurostimulation, particularly spinal cord stimulation (SCS) therapies are not efficacious for all patients. Prior to receiving a permanent implant, it is common practice to utilize a screening approach to evaluate which patients respond to therapy. The screening commonly consists of two phases: intraoperative lead placement testing in a surgical procedure room and an efficacy trial phase during which the pulse generator is worn by the patient outside of a clinical setting.

Intraoperative testing is an acute evaluation of the integrity of the implanted electrode leads used for delivering stimulation and adequacy of a positioning of the electrode leads. Intraoperative testing is performed during the placement of the temporary electrode leads (for a trial) and permanent leads (for a permanent implant).

During the trial phase, the pulse generator being connected to the electrode leads is affixed to the patient, who continues to wear the pulse generator during normal daily activities. During this time the delivery of therapy by the pulse generator can be adjusted and the efficacy of the therapy can be evaluated.

Figure 1:
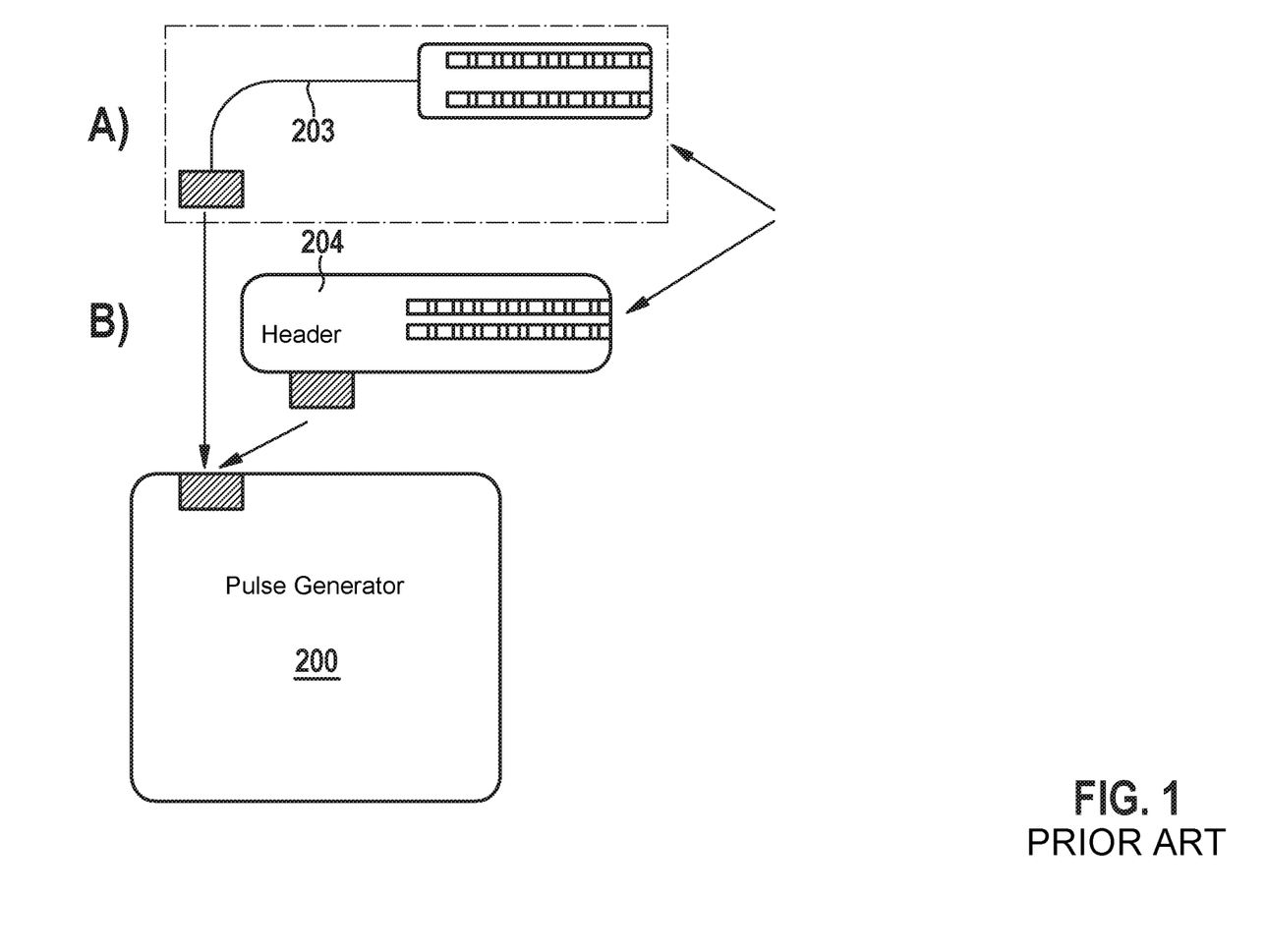
FIG. 1 is a schematic illustration of a set-up of a pulse generator and electrode leads connected to the pulse generator during intraoperative testing (A) and during a trial phase (B)

In the prior art, solutions for implementing intraoperative testing as well as trial phase stimulation are known which follow the paradigm shown in FIG. 1.

Here, prior to implantation of the whole spinal cord stimulation system, the patient wears a trial stimulator for about seven (7) days in order to see whether spinal cord stimulation is effective or not. The trial stimulator is an externally worn pulse generator 200 which is connected to the implanted electrode lead pin connectors 201, 202.

In the surgery procedure, the physician implants the two electrode leads 201, 202. In the next step, the stimulation parameter settings for the patient need to be found. For this purpose, the proximal ends of the electrode leads 201, 202 which are outside of the patient's body are first connected to multi-lead trial cable 203 and the multi-lead trial cable 203 is connected to the external pulse generator 200. The pulse generator 200 can then be programmed using a programmer device and the system can be tested to find an optimal setting of stimulation parameters. Afterwards, the multi-lead trial cable is disconnected from the pulse generator and the electrode leads are disconnected from the multi-lead trial cable. A header 204 is now connected to the external pulse generator 200 and the electrode leads 201, 202 are inserted into the header 204. The external pulse generator 200 is now worn by the patient during the trial phase.

Another solution involves a disposable pulse generator with integral lead interface.

Finally, solutions are also known where a cable used in intraoperative testing remains in place between the pulse generator and the electrode leads for the duration of the patient-worn trialing period.

Thus, existing systems often contain two adapting devices (e.g. the multi-lead trial cable and the header described above), which duplicate interfacing the proximal end of the leads to an externally worn pulse generator, which has potential disadvantages related to cost and waste. Furthermore, unplugging and re-plugging the leads from the multi-lead trial cable into the header of the external pulse generator, increases the likelihood of poor connections, as impedance must be re-checked with each new connection and also increases handling of the percutaneous electrode leads during additional disconnection and re-connection, potentially leading to damage to the respective electrode lead.

Furthermore, solutions that require the use of long cables in the trial phase for connecting the electrode leads to the external pulse generator have the risk of becoming snagged or disconnected from the pulse generator or from the electrode leads; potentially resulting in failed or aborted trials.

In addition to these challenges, the first step that a clinician takes after attaching leads to the test cable is to perform an impedance test to verify connection and lead integrity. This involves requesting test execution from a non-sterile programmer instrument operator, the operator running the test, and relaying the result verbally back to the clinician. This induces additional waiting time for the clinician and the chance of miscommunication, frequent re-testing requests if there is an impedance issue.

SUMMARY OF THE INVENTION

Based on the above, it is an objective of the present invention to provide an adapter system that reduces the above-described difficulties.

To this end, an adapter system for adapting a pulse generator to implantable electrode leads is disclosed, containing:

a) a pulse generator configured to generate electrical stimulation pulses, wherein the pulse generator comprises a connector member;

b) an adapter, wherein the adapter comprises a housing itself comprising two receptacles, wherein each receptacle is configured to receive a the proximal end portion of an electrode lead in order to establish an electrical connection between the adapter and the electrode lead when the end portion of the electrode lead is received in the receptacle, and wherein the adapter comprises a connector member configured to engage with the connector member of the pulse generator to establish a mechanical connection between the housing of the adapter and the pulse generator as well as an electrical connection between the pulse generator and the respective electrode lead when the end portion of the respective electrode lead is received in the respective receptacle; and c) a single-use test cable for electrically connecting the pulse generator to the electrode leads (e.g. for the purpose of testing the electrode leads after implantation of the electrode leads), wherein the test cable comprises a first connector member configured to engage with the connector member of the adapter to establish an electrical connection between the test cable and the electrode leads via the adapter, and wherein the test cable comprises a second connector member configured to engage with the connector member of the pulse generator to establish an electrical connection between the test cable and the pulse generator.

Particularly, at least one electrical contact is provided in each receptacle of the housing of the adapter, wherein the at least one electrical contact is configured to contact an electrical contact of an electrode lead when an end portion of the electrode lead is received in the receptacle. Particularly, for example when the respective electrode lead comprises eight electrode contacts, eight electrical contacts are provided in each receptacle for contacting corresponding electrical contacts of the respective electrode.

Furthermore, according to an embodiment of the adapter system, the pulse generator is an external pulse generator (EPG) that is configured to be worn by a patient outside the patient's body.

Further, according to a preferred embodiment, also the adapter is an external adapter that is configured to be arranged outside the patient's body (e.g. worn by the patient outside the patient's body).

Furthermore, according to an embodiment of the adapter system, the connector member of the adapter is a shrouded connector. Furthermore, according to an embodiment, the second connector member of the test cable is a shrouded connector.

Furthermore, according to an embodiment of the adapter system, the connector member of the pulse generator forms a receptacle configured to receive the shrouded connector of the adapter (e.g. during the trial phase) or the shrouded connector of the test cable (e.g. during intraoperative testing).

Furthermore, according to an embodiment, the first connector member of the test cable forms a receptacle configured to receive the shrouded connector of the adapter (e.g. during intraoperative testing).

Furthermore, according to an embodiment of the adapter system, the test cable comprises a docking body at an end of the test cable, wherein the docking body comprises the first connector member (e.g. receptacle) of the test cable, and wherein the housing of the adapter is configured to be releasably fastened to the docking body when the connector member of the adapter is engaged with the first connector member of the test cable.

Furthermore, according to an embodiment of the adapter system, the docking body comprises a latching member configured to releasably fasten the housing of the adapter to the docking body of the test cable when the connector member of the adapter is engaged with the first connector member of the test cable.

Furthermore, according to an embodiment of the adapter system, the docking body comprises a bottom surface and lateral surface extending perpendicular to the bottom surface, wherein the first connector member of the test cable is provided on the bottom surface, wherein particularly the first connector member comprises a receptacle formed in the bottom surface, which receptacle is configured to receive the connector member (e.g. shrouded connector) protruding from the housing of the adapter.

Furthermore, according to an embodiment of the adapter system, the docking body comprises at least one guide rail configured to guide the housing of the adapter upon engagement of the connector member of the adapter with the first connector of the test cable. Particularly, the at least one guide rail is configured to engage with a groove formed in the housing of the adapter.

Furthermore, according to an embodiment of the adapter system, the housing of the adapter is configured to be arranged in a form fitting manner with respect to the docking body when the connector member of the adapter is engaged with the first connector of the test cable.

Furthermore, according to an embodiment of the adapter system, the test cable comprise a pivotable cover element mounted to the docking body. The cover element is configured to be pivoted between an open position and a closed position and the cover element is configured to allow engagement of the connector member of the adapter with the first connector of the test cable when the cover element is in the open position. The cover element is configured to cover the housing of the adapter when the cover element is in the closed position and the connector member of the adapter is engaged with the first connector member of the test cable. According to an embodiment, the pivotable cover element comprises transparent or semi-transparent material.

Furthermore, according to an embodiment of the adapter system, the pulse generator comprises an impedance measuring circuit configured to periodically measure impedances of electrode leads connected to the adapter via the receptacles formed in the housing of the adapter, wherein particularly the circuit is configured to measure the respective impedance along a measurement path from the pulse generator to a tissue-interfacing electrode contact of the respective electrode lead.

Furthermore, according to an embodiment of the adapter system, the test cable comprises two indicators. A respective indicator is configured for indicating an impedance status of an electrode lead connected to the adapter. The circuit is configured to indicate via the respective indicator, if a measured impedance of the respective electrode lead lies within a pre-defined range. The respective indicator can be an optical indicator comprising a light source, e.g. an LED, or other indicator such as an auditory indicator.

Furthermore, according to an embodiment of the adapter system, the indicators are arranged on the docking body.

Furthermore, according to an embodiment of the adapter system, the adapter system comprises a further cable for electrically connecting the pulse generator to the electrode leads during a trial phase. The further cable comprises a first connector member configured to engage with the connector member of the adapter to establish an electrical connection between the further cable and the electrode leads via the adapter. The further cable comprises a second connector member configured to engage with the connector member of the pulse generator to establish an electrical connection between the further cable and the pulse generator. The further cable comprises a length that is smaller than a length of the test cable. Thus, using the longer test cable during intraoperative testing allows to keep the pulse generator out of the area in which surgery is performed, while the shorter further cable allows the patient to wear the external pulse generator during a trial phase, wherein the risk of entangling the cable is reduced due to its shorter length. Further, the reduced length of the further cable also makes carrying the further cable more comfortable.

According to yet another aspect of the present invention, a neurostimulation system is disclosed, wherein the neurostimulation system comprises an adapter system according to the present invention, and wherein the neurostimulation system comprises two electrode leads. Each electrode lead comprises an end portion, and wherein the neurostimulation system comprises an adapter system according to one of the preceding claims. Each receptacle is configured to receive an end portion of one of the electrode leads of the neurostimulation system to establish an electrical connection between the adapter and the respective electrode lead when the end portion of the respective electrode lead is received in the respective receptacle.

According to an embodiment of the neurostimulation system, the electrode leads are configured for spinal cord stimulation. Particularly, each electrode lead may comprise eight electrode contacts for applying electrical stimulation pulses generated by the pulse generator to the spinal cord of the patient.

Other features which are considered as characteristic for the invention are set forth in the appended claims.

Although the invention is illustrated and described herein as embodied in a modular neurological screening adapter system for intraoperative testing and patient-worn trialing, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIGS. 6A-6C are perspective views of a further embodiment of an adapter system according to the present invention, wherein FIGS. 6A and 6B show the adapter connected to the docking body of the test cable and FIG. 6C shows the adapter being connected to the pulse generator.

DETAILED DESCRIPTION OF THE INVENTION

Figure 2A:
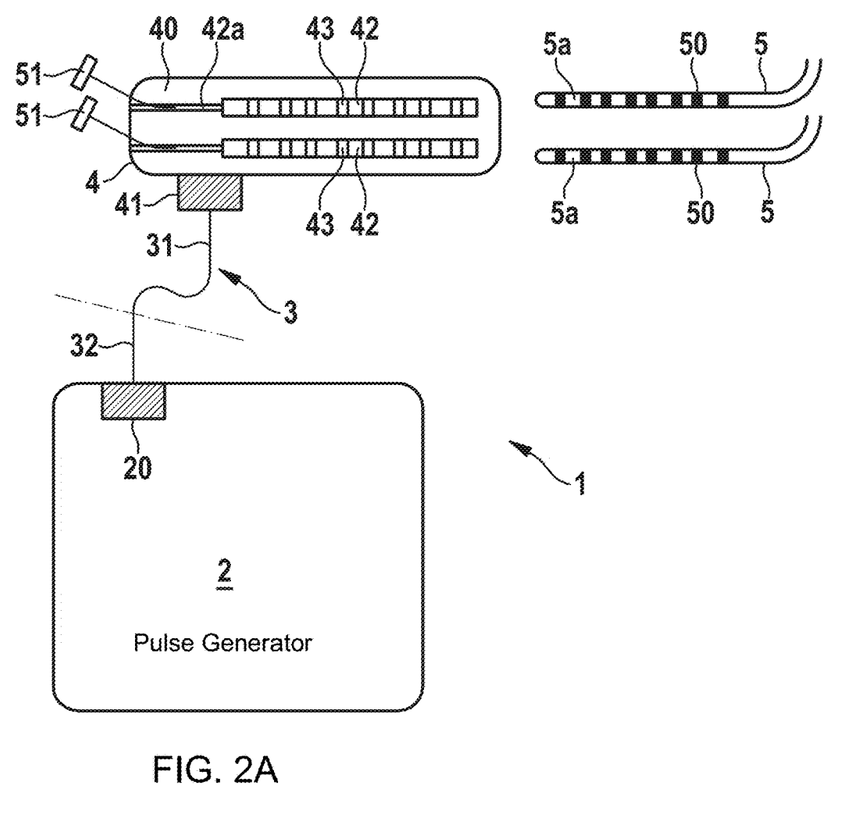
FIGS. 2A and 2B are schematic illustrations of an embodiment of an adapter system according to the present invention, wherein the adapter system comprises an adapter connecting the electrode leads via an intraoperative test cable to the pulse generator during intraoperative testing (FIG. 2A), and wherein the adapter is directly connected to the pulse generator during a trial phase thereafter (FIG. 2B)
Figure 2B:
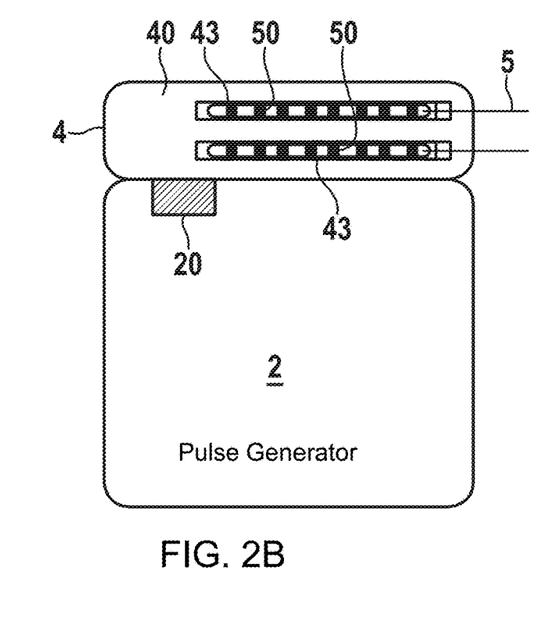

Referring now to the figures of the drawings in detail and first, particularly to FIGS. 2A-2B thereof, there is shown an adapter system 1 for adapting an e.g. externally worn pulse generator (EPG) to implanted percutaneous electrode leads 5.

Particularly, according to an embodiment shown in FIGS. 2A-2B, the adapter system 1 comprises a pulse generator 2, particularly an external pulse generator (EPG) 2, that is configured to be carried by the patient outside the patient's body, an (intraoperative) test cable 3, and an external adapter 4, that is particularly used for both intraoperative testing (shown in FIG. 2A) and during the trial phase (shown in FIG. 2B) in which the patient wears the pulse generator 2 connected to the implanted electrode leads 5 through the external adapter 4. Preferably, the external adapter 4 is configured to dock to the EPG for trialing after removal of the intraoperative test cable 3.

Particularly, intraoperative testing is an acute evaluation of the integrity of the implanted electrode leads 5 used for delivering stimulation and adequacy of a positioning of the electrode leads 5 while in a surgical setting. Furthermore, particularly, the EPG 2, intraoperative test cable 3 and the external adapter 4 are used to perform the intraoperative testing. The external adapter 4 and the mated intraoperative test cable 3 connects the EPG 2 to the electrode leads 5, while at the same time allowing the EPG 2 to remain outside of the surgical sterile field. Intraoperative testing is performed during the placement of the temporary electrode leads 5 (for a trial) and permanent electrode leads 5 (for a permanent implant). Intraoperative test cables have typical lengths of e.g. 2 m. The adapter 4 is continued to be used to interface to the electrode leads in the trial phase, described below. Particularly, when intraoperative testing is completed, the intraoperative test cable 3 is removed and can be discarded or pre-processed.

Particularly, in the trial phase, the EPG 2 and mated adapter 4 is affixed via dressings to the patient. The EPG 2 is e.g. affixed to the patient for a trial consisting between 3-30 days. The patient continues to wear the EPG 2 during normal daily activities. During this time a patient remote control can be used to adjust therapy and to collect patient input feedback related to pain relief (e.g. surveys). Meanwhile, the EPG 2 may autonomously collect statistics related to stimulation therapy usage patterns. These statistics can be telemetered from the EPG 2 to the patient's remote control e.g. via radio communication (e.g. Bluetooth or MICS).

Particularly, as shown in FIGS. 2A-2B, the EPG 2 comprises a connector member 20, which can be formed as a receptacle 20. Further, particularly, the external adapter 4 comprises a housing 40 comprising two receptacles 42, wherein each receptacle 42 is configured to receive an end portion 5a of one of the electrode leads 5 to establish an electrical connection between the adapter 4 and the electrode leads 5.

Particularly, electrical contacts 43 are provided in each receptacle 42 of the housing 40 of the external adapter 4, that are configured to contact corresponding electrical contacts 50 of the respective electrode lead 5 when the end portion 5a of the electrode lead 5 is received in the respective receptacle 42. Particularly, in case the respective electrode lead 5 comprises eight electrode contacts to apply electrical stimulation (not shown), eight electrical contacts 43 are provided in each receptacle 42.

Furthermore, each receptacle 42 of adapter 4 is adjacent to a channel 42a of the housing 40. There is a passage between the cavity formed by a receptacle and the adjacent channel 42a, via which stylets 51 can be pulled out of the lumen of the electrode leads 5 after implantation of the latter.

Further, the external adapter 4 comprises a connector member 41 that at the housing 40 of the external adapter 4 and forms a shrouded connector 41 configured to engage with the connector member 20 of the pulse generator 2 to establish a mechanical connection between the housing 40 of the external adapter 4 and the pulse generator 2 as well as an electrical connection between the pulse generator 2 and the respective electrode lead 5. Preferably, the connector member 20 of the EPG 2 is formed as a receptacle 20 for receiving shrouded connector 41 of the adapter 4.

Further, particularly, the test cable 3 is configured for electrically connecting the pulse generator 2 to the electrode leads 5 through the external adapter 4 for the specific purpose of intraoperative testing the electrode leads 5 after implantation of the electrode leads 5 as described above. The test cable 3 comprises a first connector member 31 configured to engage with the connector member 41 of the adapter 4 to establish an electrical connection between the test cable 3 and the electrode leads 5 through the adapter 4. Preferably, the first connector member 31 is formed as a receptacle forming the same electrical docking interface as the connector member 20 of the EPG 2. Furthermore, the test cable 3 comprises a second connector member 32 configured to engage with the connector member 20 of the pulse generator 2 to establish an electrical connection between the test cable 3 and the pulse generator 2. Preferably, the second connector member 32 of the test cable 3 is a shrouded connector 32 forming the same electrical docking interface as the connector member 41 of the adapter 4.

Figure 3:
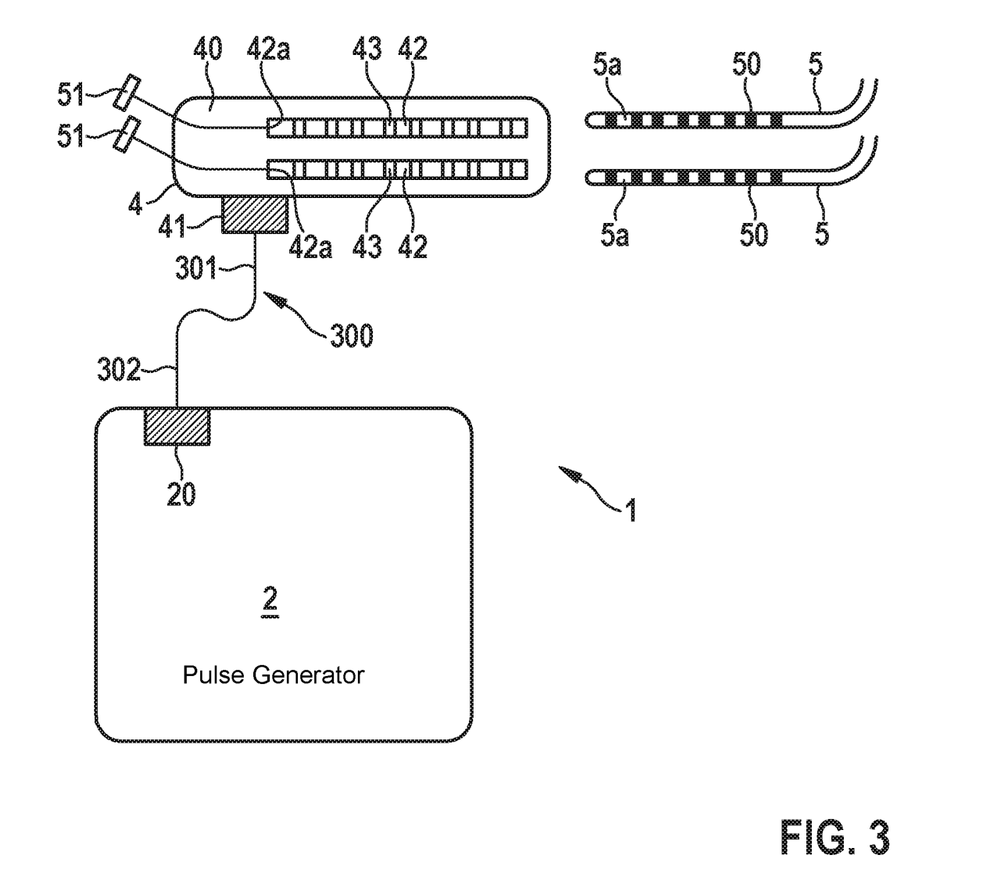
FIG. 3 is a schematic view showing a modification of the embodiment shown in FIG. 2, wherein in contrast to FIG. 2 the adapter is connected via a further, albeit short cable, to the pulse generator during the trial phase.
Figure 4:
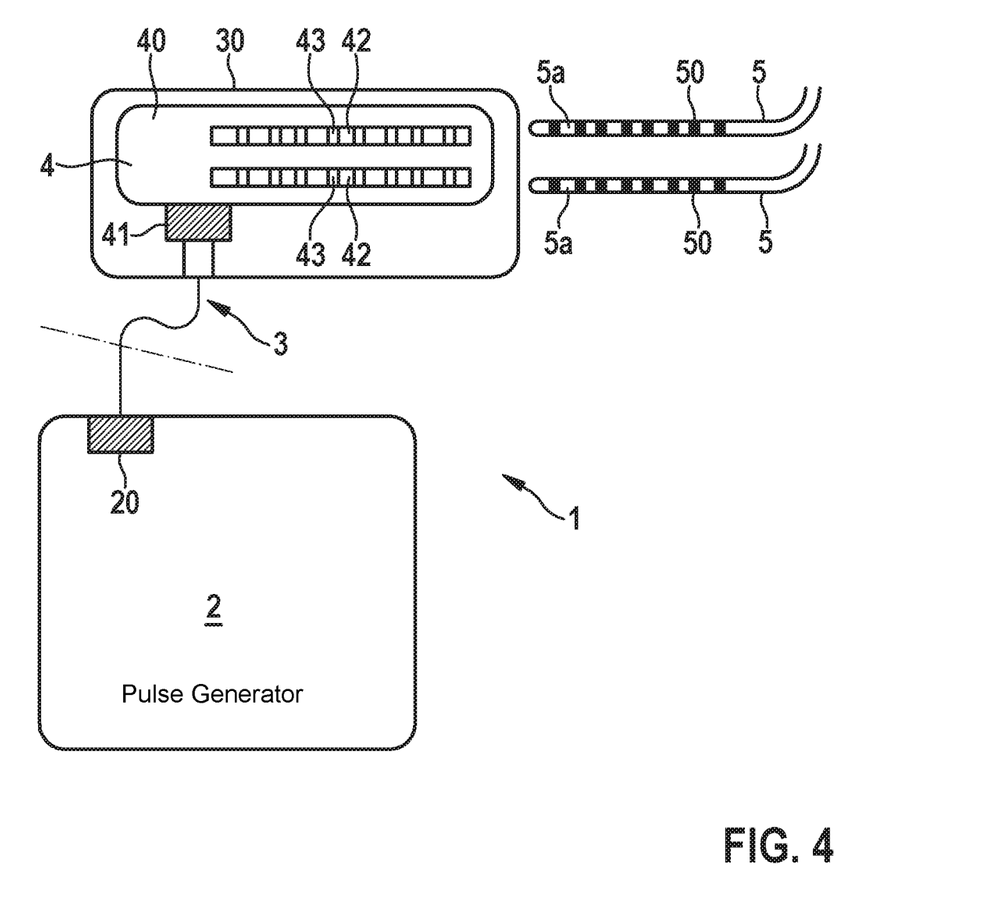
FIG. 4 is a schematic view of a further embodiment of the adapter system according to the present invention, wherein the test cable comprises a docking body for receiving the adapter.

FIG. 3 shows a modification of the adapter system 1 according to the present invention, wherein the test cable 3 is available in an additional, shorter length in the axial direction of the cable. The further cable 300 can be used in conjunction with the external adapter 4 during the patient-worn trial phase, in the event that the patient or physician wishes to locate the EPG 2 at a more distant location from the lead exit site (such as on the patient's side). Also here, the further cable comprises a first connector member 301 to engage with the connector member 40 of the adapter, and a second connector member 302 to engage with the connector member 20 of the EPG 2. Also here, preferably, the first connector member 301 is a receptacle, and the second connector member 302 is a shrouded connector 302.

In further embodiments, shown in FIGS. 4 to 6C, the test cable 3 includes on its distal (to the EPG 2) terminus a docking body 30 for the external adapter 4, which augments the graspable physical size of the test cable 3. Particularly, the docking body 30 is removable from the external adapter 4. The docking body 30 may be integral to the terminus of the intraoperative test cable 3 or may be designed as a snap-in floating piece. This allows for improved grip and usability in the intraoperative portion without impairing a compact trial phase.

Figure 5A:
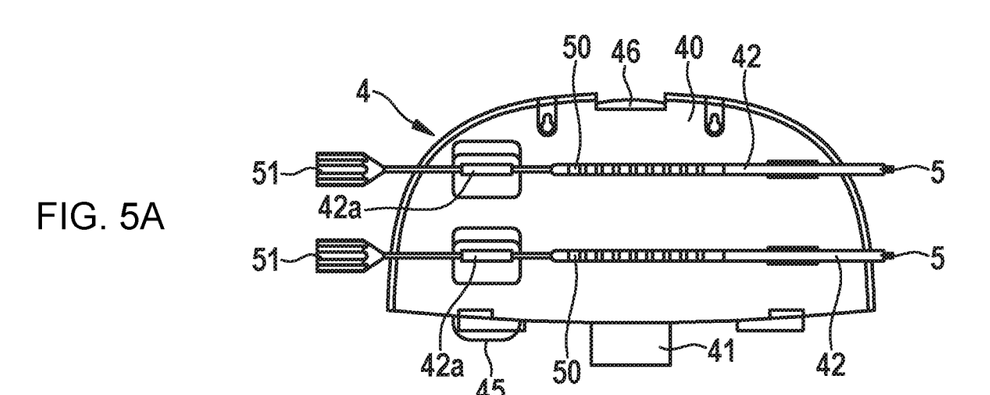
FIGS. 5A-5C are side views of an embodiment of an adapter (FIG. 5A) and of a corresponding docking body of the test cable (FIG. 5B) as well as a perspective view of the docking body (FIG. 5C)
Figure 5B:
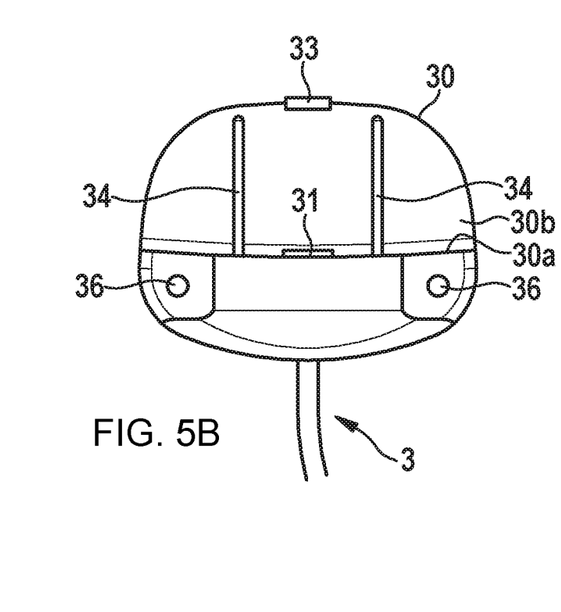
Figure 5C:
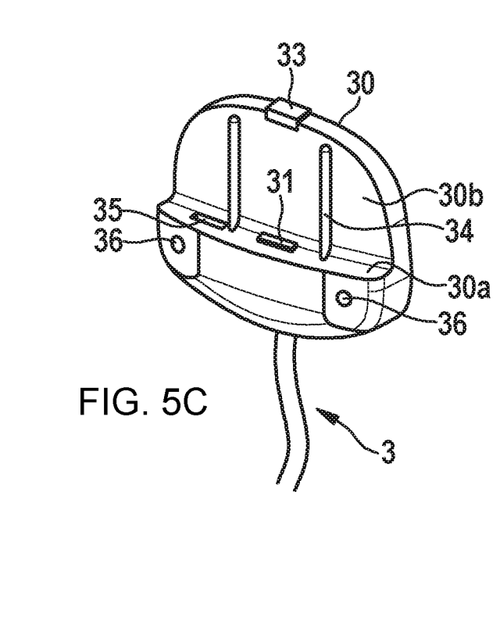

Particularly, as indicated in FIGS. 5A-5C, the housing 40 of the external adapter 4 is configured to be releasably fastened to the docking body 30 when the connector member 41 of the external adapter 4 is engaged with the first connector member 31 of the test cable 3. Particularly, to this end, the docking body 30 comprises a latching member 33 configured to releasably fasten the housing 40 of the adapter 4 to the docking body 30 of the test cable 3 when the connector member 41 of the adapter 4 is engaged with the first connector member 31 of the test cable 3. Particularly, the latching member 33 may be configured to engage behind an edge region 46 of the housing 40 of the adapter 4 to releasably fasten the housing 40 to the docking body 30.

Particularly, the docking body 30 can comprise a bottom surface 30a and lateral surface 30b extending perpendicular to the bottom surface 30a, wherein the first connector member 31 of the test cable is a receptacle 31 formed in the bottom surface 30a.

Further, for guiding the housing 40 of the adapter 4 upon engagement of the connector member 41 of the adapter 4 with the first connector member 31 (e.g. receptacle) of the test cable 3, the docking body 30 can comprise at least one guide rail 34 formed on the lateral surface 30b of the docking body 30. Furthermore, the adapter 4 may comprise a protrusion 45 protruding from the housing 40 of the adapter 4, which protrusion 45 is configured to be inserted into a corresponding recess 35 formed in the bottom surface 30 of the docking body 30 to e.g. ensure that the connector members 31 and 41 are mated in the correct orientation.

Particularly, the surfaces 30a, 30b are configured to support the housing 40 of the adapter 4 and are particularly designed such that the housing 40 is arranged in a form fitting manner with respect to the docking body 30 when the connector member 41 of the adapter 4 is engaged with the first connector member/receptacle 31 of the test cable 3.

Figure 7:
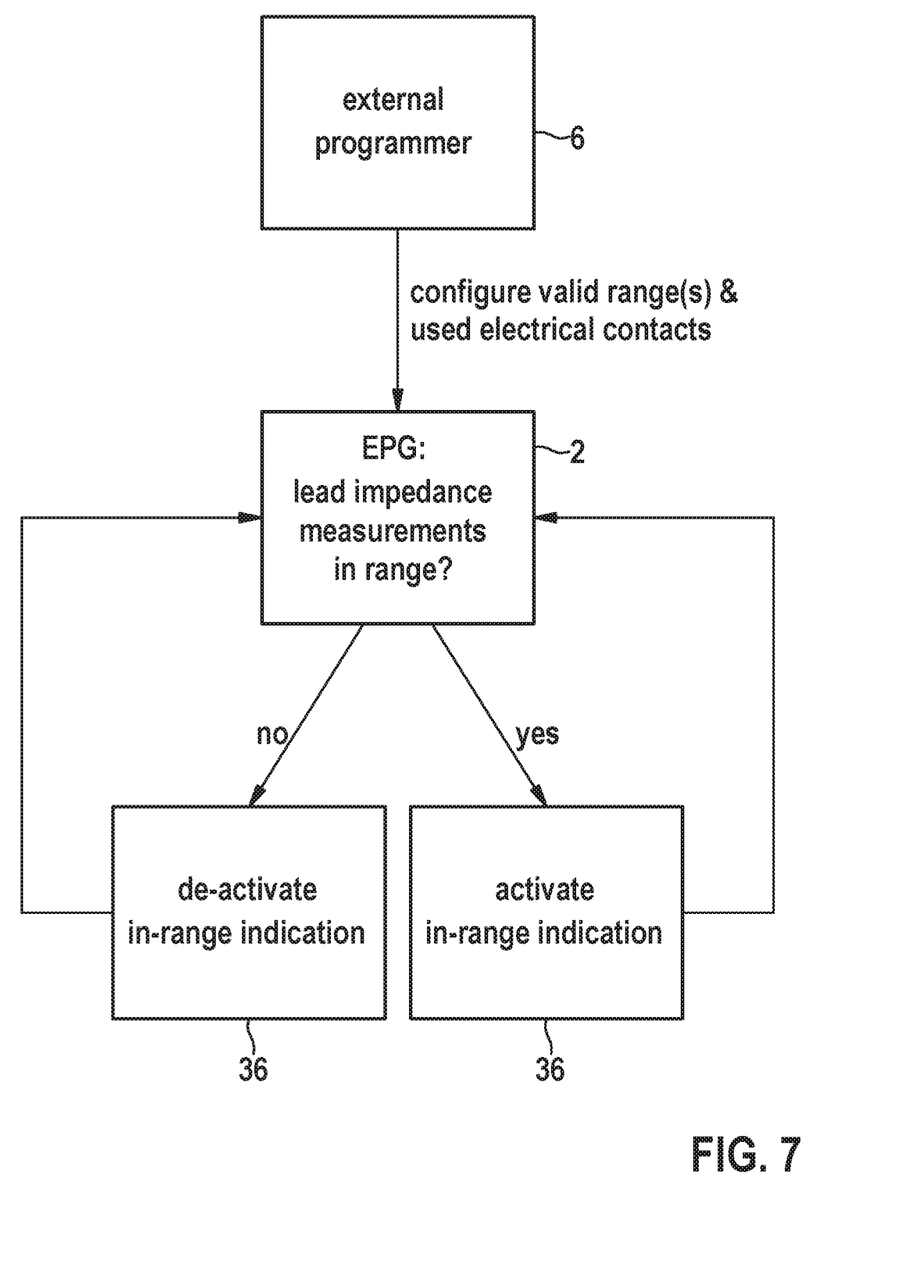
FIG. 7 is a block diagram relating to the display of an impedance indicator as measured by the EPG.

According to a further embodiment, as shown in FIGS. 5A-5C in conjunction with FIG. 7, the docking body 30 comprises (e.g. optical) several indicators 36. Particularly, the respective indicator 36 is connected via a pair of conductors (e.g. wires) inside the intraoperative test cable 3 to the EPG 2 (when test cable 3 and EPG 2 are connected) and electrically activatable. Furthermore, the EPG 2 preferably includes an impedance measuring circuit for measuring of the lead impedance of all or utilized electrical stimulation contacts (including all connections). Particularly, the measurement path extends from the EPG 2 to the implanted electrode lead 5, thus encompassing the impedance of all connections along the path. Particularly, the EPG 2 is configured to perform periodic impedance measurements and activates indicator(s) 36 when the impedance of configurable electrode contacts (not shown) of the electrode lead 5 is within a programmed range. The respective indicator 36 is particularly deactivated or altered when the impedance is outside of the programmed range (e.g. too high or too low). Particularly, the indicators 36 can be used when programming the EPG 2 using an external programmer 6 as shown in FIG. 7.

Particularly, the respective indicator 36 can be a multi-color indicator. Furthermore, instead of optical indicators 36, the respective indicator can also be one of: an audible indicator, an alphanumeric indicator, a tactile indicator.

Furthermore, according to an embodiment, the respective indicator (and the circuit 21) can be configured to measure/indicate one of: a tri-state electrode lead impedance (e.g. poor, fair, good), a relative lead positioning (indicating which electrode lead 5 is in superior location relative to other electrode lead 5), a neural response (indicating when sensed neural responses are in range or out of range to assist electrode lead positioning).

Figure 6A:
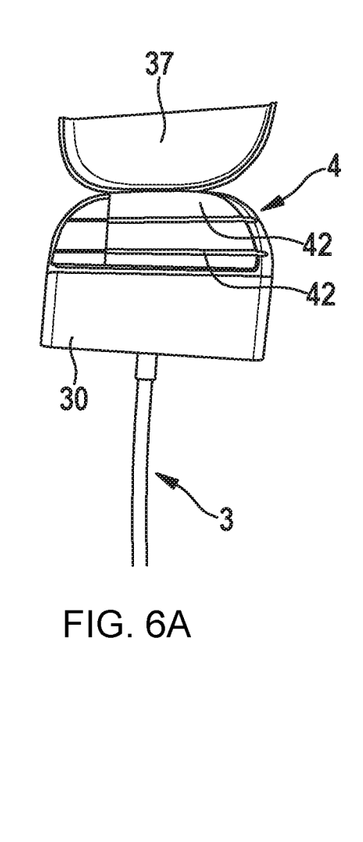
Figure 6B:
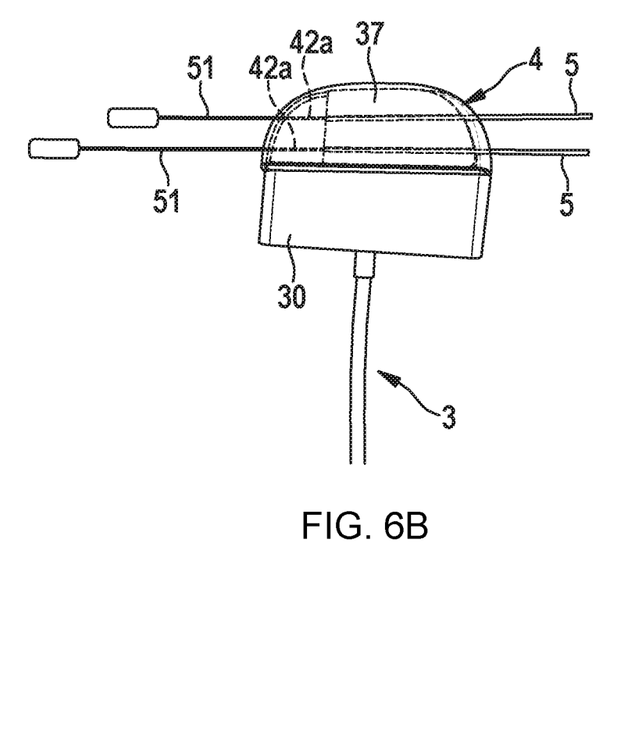
Figure 6C:
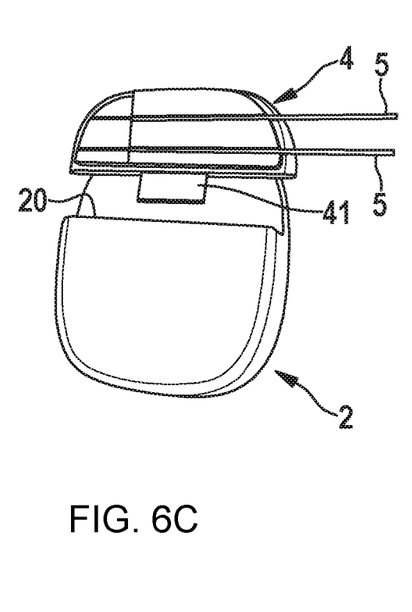

FIGS. 6A-6C show a further embodiment of an adapter system 1 according to the present invention, wherein here the test cable 3 comprises a pivotable cover element 37 mounted to the docking body 30. The cover element 37 is configured to be pivoted between an open position and a closed position, wherein the cover element 37 is configured to allow engagement of the connector member 41 of the external adapter 4 with the first connector member 31 of the test cable 3 when the cover element 37 is in the open position (FIG. 6A). The cover element 37 is configured to cover the housing 40 of the adapter 4 when the cover element 37 is in the closed position (FIG. 6B) and the connector member 41 of the adapter 4 is engaged with the first connector member 31 of the test cable 3. Particularly, the cover element can be transparent or can comprise a transparent portion. FIG. 6C shows insertion of the connector member 41 (e.g. shrouded connector) of the adapter 4 into the connector member 20 (e.g. receptacle) of the EPG 2.

The re-use of the external adapter 4 is beneficial due to the fact that is lowers costs and improves handling of the system in a surgical environment without compromising the trial phase during which the person wears the EPG 2. Furthermore, indication at the patient end of the external adapter 4 of proper electrode lead impedance provides direct feedback to the implanting clinician, and allows improved positioning of the electrode leads 5.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

The invention claimed is:

1. An adapter system for connecting to implantable electrode leads, the adapter system comprising:
   a pulse generator configured to generate electrical stimulation pulses and having a connector member;
   an adapter having a housing with two receptacles, wherein each of said receptacles configured to receive an end portion of an electrode lead to establish an electrical connection between said adapter and the electrode lead, said adapter additionally having a connector member on said housing, said connector member of said adapter configured to engage with said connector member of said pulse generator to establish a mechanical connection between said housing of said adapter and said pulse generator as well as an electrical connection between said pulse generator and the electrode lead; and
   a test cable for electrically connecting said pulse generator to the electrode leads for testing the electrode leads after implantation of the electrode leads, said test cable having a first connector member configured to removably engage with said connector member of said adapter to establish an electrical connection between said test cable and the electrode leads through said adapter, and said test cable having a second connector member configured to engage with said connector member of said pulse generator to establish an electrical connection between said test cable and said pulse generator.

2. The adapter system according to claim 1, wherein said pulse generator is an external pulse generator configured to be disposed outside a body of a patient.

3. The adapter system according to claim 1, wherein:
   said connector member of said adapter is a shrouded connector; and/or
   said second connector member of said test cable is a shrouded connector.

4. The adapter system according to claim 1, wherein:
   said connector member of said pulse generator is a receptacle; and/or
   said first connector member of said test cable is a receptacle.

5. The adapter system according to claim 1, wherein:
   said test cable contains a docking body having said first connector member of said test cable; and
   said housing of said adapter is configured to be releasably fastened to said docking body when said connector member of said adapter is engaged with said first connector member of said test cable.

6. The adapter system according to claim 5, wherein said docking body contains a latching member configured to releasably fasten said housing of said adapter to said docking body of said test cable when said connector member of said adapter is engaged with said first connector member of said test cable.

7. The adapter system according to claim 5, wherein:
   said docking body has a bottom surface and a lateral surface extending perpendicular to said bottom surface; and
   said first connector member of said test cable is a receptacle formed in said bottom surface.

8. The adapter system according to claim 7, wherein said docking body contains at least one guide rail configured to guide said housing of said adapter upon engagement of said connector member of said adapter with said first connector member of said test cable.

9. The adapter system according to claim 5, wherein said housing of said adapter is configured to be disposed in a form fitting manner with respect to said docking body when said connector member of said adapter is engaged with said first connector member of said test cable.

10. The adapter system according to claim 5, wherein:
    said test cable has a pivotable cover element mounted to said docking body;
    said pivotable cover element is configured to be pivoted between an open position and a closed position;
    said pivotable cover element is configured to allow engagement of said connector member of said adapter with said first connector member of said test cable when said pivotable cover element is in the open position; and
    said pivotable cover element is configured to cover said housing of said adapter when said pivotable cover element is in the closed position and said connector member of said adapter is engaged with said first connector member of said test cable.

11. The adapter system according to claim 5, wherein:
    said pulse generator has an impedance measuring circuit configured to periodically measure impedances of the electrode leads connected to said adapter via said receptacles; and
    said impedance measuring circuit is configured to measure a respective impedance along a measurement path from said pulse generator to an electrode contact of the electrode lead.

12. The adapter system according to claim 11, wherein:
    said test cable has two indicators disposed on said docking body; and
    said impedance measuring circuit is configured to indicate via a respective one of said indicators, if a measured impedance of the electrode lead lies within a predefined range.

13. The adapter system according to claim 1, further comprising:
    a further cable exchangeable with said test cable when said test cable is disconnected from said pulse generator and said adaptor, said further cable for electrically connecting said pulse generator to the electrode leads during a trial phase, said further cable having a first connector member configured to engage with said connector member of said adapter to establish an electrical connection between said further cable and the electrode leads through said adapter, wherein said further cable having a second connector member configured to engage with said connector member of said pulse generator to establish an electrical connection between said further cable and said pulse generator, and wherein said further cable having a length that is smaller than a length of said test cable.

14. A neurostimulation system, comprising:
two electrode leads each having an end portion; and
an adapter system, containing:
  a pulse generator configured to generate electrical stimulation pulses and having a connector member;
  an adapter having a housing with two receptacles, wherein each of said receptacles receives said end portion of an electrode lead of said electrode leads to establish an electrical connection between said adapter and said electrode lead, said adapter additionally having a connector member on said housing, said connector member of said adapter configured to engage with said connector member of said pulse generator to establish a mechanical connection between said housing of said adapter and said pulse generator as well as an electrical connection between said pulse generator and said electrode lead; and
  a test cable electrically connecting said pulse generator to said electrode leads for testing said electrode leads after implantation of said electrode leads, said test cable having a first connector member configured to removably engage with said connector member of said adapter to establish an electrical connection between said test cable and said electrode leads through said adapter, and said test cable having a second connector member configured to engage with said connector member of said pulse generator to establish an electrical connection between said test cable and said pulse generator.

15. The neurostimulation system according to claim 14, wherein said electrode leads are configured for spinal cord stimulation.

16. The neurostimulation system according to claim 14, further comprising:
  a further cable exchangeable for said test cable, said further cable for electrically connecting said pulse generator to the electrode leads during a trial phase, said further cable having a first connector member configured to engage with said connector member of said adapter to establish an electrical connection between said further cable and the electrode leads through said adapter, said further cable having a second connector member configured to engage with said connector member of said pulse generator to establish an electrical connection between said further cable and said pulse generator, and said further cable having a length that is smaller than a length of said test cable.

* * * * *